(12) United States Patent
Abeygunaratne

(10) Patent No.: US 7,674,610 B2
(45) Date of Patent: Mar. 9, 2010

(54) METHOD AND DEVICE FOR PROBING CHANGES IN A MEMBRANE BY APPLYING AN IN-PLANE ELECTRIC FIELD

(76) Inventor: Thusara Sugat Chandra Abeygunaratne, 2288 Norman Dr., Stow, OH (US) 44224

( * ) Notice: Subject to any disclaimer, the term of this patent is extended or adjusted under 35 U.S.C. 154(b) by 664 days.

(21) Appl. No.: 11/400,685

(22) Filed: Apr. 7, 2006

(65) Prior Publication Data

US 2007/0259331 A1    Nov. 8, 2007

(51) Int. Cl.
*C12M 1/34* (2006.01)
(52) U.S. Cl. .............................. 435/173.4; 435/4; 435/29
(58) Field of Classification Search ....................... 435/4, 435/29, 173.4
See application file for complete search history.

(56) References Cited

U.S. PATENT DOCUMENTS

| 5,321,533 | A   |   | 6/1994  | Kumar        |       |
|-----------|-----|---|---------|--------------|-------|
| 5,670,322 | A   | * | 9/1997  | Eggers et al. | 506/3 |
| 6,627,396 | B1  |   | 9/2003  | Swanson et al. |      |
| 2004/0214312 | A1 |   | 10/2004 | Tyvoll et al. |      |
| 2005/0011256 | A1 |   | 1/2005  | Hoh          |       |
| 2006/0216740 | A1 | * | 9/2006  | Edman et al. | 435/6 |

OTHER PUBLICATIONS

Wiki (http://lamp.tu-raz.ac.at/%7Ehadley/nanoscience/glossary.html), Printed Apr. 25, 2009.*
Baudry et al. 2001. Molecular Dynamics Study of Bacteriorhodopsin and the Purple Membrane. The Journal of Physical Chemistry B, vol. 105, No. 5, pp. 905-918.*
Groves, Jay T., et al., "Micropatterning fluid lipid bilayers on solid supports", Science, vol. 275, Jan. 31, 1997, pp. 651-653.
Boxer, Steven G., "Molecular transport and organization in supported lipid membranes", Current Opinion in Chemical Biology 2000, 4:704-709.
Pantoja, Rigo, et al., "Bilayer reconstitution of voltage-dependent ion channels using a microfabricated silicon chip", Biophysical Journal, vol. 81, Oct. 2001, pp. 2389-2394.
Abeygunaratne, S., et al., "Evidence for uncorrelated tilted layer structure and electrically polarized bilayers in amphiphilic glycolipids", Physical Review E73, 011916 (2006), pp. 011916-1-011916-6.
Sackmann, E., "Supported membranes: scientific and practical applications", Science, New Series, vol. 271, No. 5245 (Jan. 5, 1996), pp. 43-48.
Groves, Jay T., et al., "Electric field-induced reorganization of two-component supported bilayer membranes", Proc. Natl. Acad. Sci. USA, vol. 94, pp. 13390-13395, Dec. 1997.
Filmore, David, "Breaching the blood-brain barrier", Modern Drug Discovery, Jun. 2002, vol. 5, No. 6, pp. 22-24, 27.
Craighead, H., et al., "Applications: biotechnology, medicine, and healthcare", Nantechnology Research Directions: IWGN Workshop Report, Sep. 1999, Chapter 8, pp. 107-120, www.wtec.org/loyola/nano/IWGN.Research.Directions/chapter08.pdf .
Fernandez, J.M., "Cellular and molecular mechanics by atomic force microscopy: capturing the exocytotic fusion pore in vivo?", Proc. Natl. Acad, Sci, USA, col. 94, pp. 9-10, Jan. 1997.
Nichii, Masayuki, et al., "Thermotropic liquid-crystalline peptide derivatives: oligo (glutamic acid)s forming hydrogen-bonded columns", Org. Biomol. Chem., 2005, 3, pp. 875-880.
Catterall, William A., "Molecular properties of voltage-sensitive sodium channels", Ann. Rev. Biochem, 1986, 55:953-985.
Guy, H. Robert, et al., "Molecular model of the action potential sodium channel", Proc. Natl. Acad. Sci. USA, vol. 83, pp. 508-512, Jan. 1986.
Jiang, Youxing, et al., "The principle of gating charge movement in a voltage-dependent K+ channel", Nature, vol. 423, May 1, 2003, www.nature.com/nature, pp. 42-48.

(Continued)

*Primary Examiner*—Jon P Weber
*Assistant Examiner*—Kailash C Srivastava
(74) *Attorney, Agent, or Firm*—Pearne & Gordon LLP

(57) ABSTRACT

The present invention is directed to disposing a membrane, for example, a biological cell membrane including amphiphilic lipids and proteins, or a liquid crystal membrane, between two electrical conductive walls having a height that is at least as great as the thickness of the membrane and, in particular, approximates the membrane thickness or height. The conductive walls are disposed on an electrically insulative base and can be approximately parallel to each other and perpendicular to the base. Two electrically conductive pads extending from each of the conductive walls are fabricated on the base. An electric field is propagated between the conductive walls along the plane of the membrane. An optional third electrode can be fabricated in between the planes of the conductive walls. This third electrode does not extend above the plane of the base and is electrically isolated from the two conducting walls. This invention relates to probing structural changes of the membrane by applying an in-plane electric field, using electric current measurements, impedance gain phase analysis, raster scanning by atomic force microscopy, and observation with confocal, fluorescence or other microscopy, but not limited to these tools.

23 Claims, 9 Drawing Sheets

OTHER PUBLICATIONS

Ahern, Christopher A., et al., "Stirring up controversy with a voltage sensor paddle", Trends in Neurosciences, vol. 27, No. 6, Jun. 6, 2004, pp. 303-307.

Bezanilla, Francisco, "The voltage sensor in voltage-dependent ion channels", Physiological Reviews, vol. 80, No. 2, Apr. 2000, pp. 555-592.

Vill, V., et al., "Thermotropic and lyotropic properties of long chain alkyl glycopyranosides, Part I: monosaccharide headgroups", Chemistry and Physics of Lipids, 104 (2000) pp. 75-91.

Jiang, Youxing, et al., "X-ray structure of a voltage-dependent K+ channel", Nature, vol. 423, May 1, 2003, www.nature.com/nature, pp. 33-41.

Singer, S.J., et al., "The fluid mosaic model of the structure of cell membranes", Science, vol. 175, pp. 720-731.

Leuchtag, H. Richard, "Fit of the dielectric anomaly of squid membrane near heat-block temperature to the ferroelectric Curie-Weiss law", Biophysical Chemistry 53 (1995) pp. 197-205.

Hodgkin, A.L., et al., "The effect of temperature on the electrical activity of the giant axon of the squid", J. Physiol. (1949) 109, pp. 240-249.

Armstrong, Clay M., et al., "Charge movement associated with the opening and closing of the activation gates of the Na channels", The Journal of General Physiology, vol. 63, 1974, pp. 533-552.

Neville, A.C., et al., "A biological system producing a self-assembling cholesteric protein liquid crystal", J. Cell Sci. 8, pp. 93-109 (1971).

Montal, M.., et al., "Formation of biomolecular membranes from lipid monolayers and a study of their electrical properties", Proc. Nat. Acad. Sci. USA, vol. 69, No. 12, pp. 3561-3566, Dec. 1972.

Sigworth, F.J., "Voltage gating of ion channels", Quarterly Reviews of Biophysics 27, 1 (1993), pp. 1-40.

Chanda, Baron, et al., "Gating charge displacement in voltage-gated ion channels involves limited transmembrane movement", Nature, vol. 436, Aug. 11, 2005, pp. 852-856.

Asamoah, Osei Kwame, et al., "A fluorometric approach to local electric field measurements in a voltage-gated ion channel", Neuron, vol. 37, pp. 85-97, Jan. 9, 2003.

Cha, Albert, et al., "Atomic scale movement of the voltage-sensing region in a potassium channel measured via spectroscopy", Nature, vol. 402, Dec. 16, 1999, pp. 809-817.

Starace, Dorine M., et al., "Voltage-dependent proton transport by the voltage sensor of the Shaker K+ channel", Neuron, vol. 19, pp. 1319-1327, Dec. 1997.

Yang, Naibo, et al., "Molecular basis of charge movement in voltage-gated sodium channels", Neuron, vol. 16, pp. 113-122, Jan. 1996.

Chang, Geoffrey, et al., "Structure of the MscL homolog from mycrobacterium tuberculosis: a gated mechanosensitive ion channel", Science, vol. 282, Dec. 18, 1998, pp. 2221-2226.

Dutzler, Raimund, et al., "X-ray structure of a CIC chloride channel at 3.0Å reveals the molecular basis of anion selectivity", Nature, vol. 415, Jan. 17, 2002, pp. 287-294.

Ellens, Harma, et al., "Fusion of phosphatidylethanolamine-containing liposomes and mechanism of the $L_\alpha$-$H_{II}$ phase transition", Biochemistry, 1986, 25, pp. 4141-4147.

Glauner, K.S., et al., "Spectroscopic mapping of voltage sensor movement in the *Shaker* potassium channel", Nature, vol. 402, Dec. 16, 1999, pp. 813-817.

DeGennes, P.G., et al., "Magnetic field effects", The Physics of Liquid Crystals, 1993, pp. 116-120.

Office Action dated Sep. 2, 2009 for U.S. Appl. No. 11/851,633, filed Sep. 7, 2007.

\* cited by examiner

METHOD AND DEVICE FOR PROBING CHANGES IN A MEMBRANE BY APPLYING AN IN-PLANE ELECTRIC FIELD

FIELD OF THE INVENTION

This invention relates to application of an electric field along the plane of a molecular membrane.

BACKGROUND OF THE INVENTION

The family of transmembrane proteins that conduct cations, $Na^+$, $K^+$, $Ca^{2+}$, and anions, $Cl^-$, $I^-$, $Br^-$, through the lipid membrane takes part in many functions fundamental to the biological cell including signal transduction. Recently, the crystal structure of the voltage dependent $K^+$ channel, KvAP, from *Aeropyrum pernix*, ClC $Cl^-$ channels from *Escherichia coli* and *Salmonella enterica serovar typhimurium* and mechanosensitive MscL channel (non selective) from *Mycobacterium tuberculosis* were determined using X-ray crystallography, biochemical and electrophysiological methods. High resolution studies of the channels reveal the ion conductive pathways and their open and closed conformations. What remains to be shown is a molecular mechanism for how the conformational change (opening and closing) in ion channels occurs in the cell-membrane.

The fourth transmembrane helix (S4) in voltage-gated channels is the primary voltage-sensing unit responsible for the opening and the closing of the channels. In molecular models such as the 'helical screw' or 'paddle' models, channels are opened and closed by a large translocation of the S4 segment in which the charged S4 residues travel across the full thickness of the lipid membrane. For example, in the paddle model, the S4 segment is buried in the lipid bilayer and traverses approximately 20 Å across the bilayer. However, accessibility data, resonance energy transfer and potentiometric studies suggest that the S4 residues move relatively small distances. Recently, it was shown that, during the gating process, the main voltage sensing element (S4) undergoes only a small movement relative to the membrane plane. It is important to note that, in all current models, membrane lipids hosting the channel proteins are considered to be dielectric and their structure is considered to play only a passive role in the conformational changes in these channel proteins.

The structure of the cell membrane in the generally accepted fluid mosaic model, a two dimensional smectic liquid crystal bilayer comprising amphiphilic lipids, cholesterol and embedded proteins, is considered to be a dielectric and to play only a passive role in the activities of the biological cell. However, there is strong evidence pointing toward an active role of the membrane in a wide range of signal transductions of the cell that can arise only from structural transition of the membrane lipids.

It has recently been observed that the amphiphilic lipid molecules are tilted in their bilayers. The tilted amphiphilic lipid layers are electrically polarized. In view of this I have made the following observations. An electric pulse along the plane of the bilayer can cause reorientation of spontaneous polarization accompanied by collective rotation of the lipid molecules. In the cell membrane, this in-plane electric pulse arises, for example, from charged residues of the transmembrane proteins. This dynamic property of the lipid membranes can be linked to signal transduction of proteins and can be investigated by applying an external in-plane electric field to the cell membrane.

In a bilayer, an in-plane component of the permanent dipole moment of one layer makes an angle with its counterpart of the opposing layer when both layers have the same tilt direction. The resulting dipole moment lies perpendicular to the tilt direction of the double layer producing a net polarization. These dipole moments can be realigned by an external electric field in a collective rotation of the molecules around a cone determined by the tilt angle of the molecules. The collective rotation of lipid molecules in a cone and the reorientation of the polarization in the lipid bilayers in cell membranes can have several effects. This can cause reversible conformational changes in membrane bound proteins and vice versa because anisotropic liquid crystals can transmit torque over a macroscopic distance. This can be expected because proteins which can be dissolved in amphiphilic lipids without disrupting the phase structure of the lipids may also exist in liquid crystalline state and it is likely that there is hydrogen bonding between proteins and the lipid head groups. The link between this reversible dynamic structural behavior of the membrane lipids and the conformational transition of the membrane bound proteins may potentially be common to all signal transductions in the biological cell.

No device has been developed to permit probing structural changes of the membrane by applying an in-plane electric field. A widely used method of preparing both symmetric and asymmetric planar membranes suitable for electrical measurements has been developed by Montal and Mueller in which an electric field can be applied perpendicular to the membrane. In this method, the bilayers are formed as a film in a small aperture on a thin Teflon septum placed between two chambers containing monolayers in an aqueous solution. The structure of the membrane formed in this apparatus is known only in the middle of the film and the structure around the vicinity of septum is not well defined. Besides this, placing the electrode on the septum is technically extremely difficult. Therefore, this method cannot be extended or modified for application of an in-plane electric field.

DISCLOSURE OF THE INVENTION

It is an object of the invention to provide a method to probe structural changes in the biological cell membrane by applying an in-plane electric field. The membrane can be extracted from a biological cell or can be formed synthetically by individual constituents of the biological cell membrane or by synthetic molecules. Subsequently, the membrane is subjected to probing its structural changes coupled to the in-plane electric field.

It is a further object of the invention to provide a nanometer scale chip with which the inventive method can be applied. A principle underlying the invention is the insight that when an in-plane electric field is applied to the membrane, the in-plane electric field causes a structural transition in the constituent molecules of the membrane.

This invention relates to probing of the structural transitions of the membrane using electric current measurements, impedance gain phase analysis, raster scanning by atomic force microscopy, and characterization of the membrane with confocal microscopy, confocal laser scanning microscopy and X-ray spectroscopy, but not limited to these tools.

This invention applies to all aspects of the biological cell membrane including the biological sciences of the biological cell membrane and medical and clinical research of the biological cell membrane. This invention also applies to characterization of membranes made of any liquid crystals even non-biological liquid crystals.

According to one aspect of the invention, to apply an electric field in the plane of the membrane, the membrane is disposed between two electrodes forming a containment region of a nanometer scale parallel plate capacitor. One side of each electrode is in a range of from about 5 to 10 nanometers ($1 \times 10^{-9}$ meter or "nm") high so that it is not less than the thickness or height of the membrane and, in particular, is approximately the same height as the membrane. The distance between the electrodes is in a range of from about 3 to 10 micrometers ($1 \times 10^{-6}$ meter or "µm"), which is suitable for propagating a sufficiently large electric field. To enable access for probing, the membrane is positioned to have a well-defined configuration with the plane of the membrane being perpendicular to the sides of the electrodes. The following are advantageous conditions at which probing of the membrane is carried out:

1. The membrane should span the entire containment volume with the plane of the membrane laying perpendicular to the sides of the electrodes.
2. The insertion of any constituents of the membrane such as transmembrane proteins should be possible at any stage of probing.
3. The surface of the membrane is advantageously accessible for probing devices such as a tip of the Atomic Force Microscope ("AFM"), a laser of the confocal microscope, and an X-ray beam, but not limited to these tools.

The nano capacitor is fabricated on a nonconducting wafer that supports extended electrical conducting pads that can be attached to electrical leads. This device is suitable for raster scanning of the membrane using atomic force microscopy, whereby the surface of the membrane spans the interior of the capacitor. The solid support of the base prevents disruption of the membrane during the probing. An optional third electrode enables measuring the gating current of channel proteins embedded in the membrane. An electric field can be applied between an electrical conductor and the third electrical conductor perpendicular to the base and the membrane surface in the containment region.

The embodiments of the invention include an apparatus, a chip and a method, for probing changes in a membrane by applying an electric field. Referring first to the apparatus embodiment, the apparatus includes a base. Electrically conductive walls are spaced apart from each other and are disposed on the base. The base and the conductive walls form a containment region that is configured to receive a membrane. The membrane has opposing surfaces. An interior plane is bounded by the membrane surfaces and extends along the membrane. The base is comprised of an electrically insulative material in the containment region adapted to support one of the membrane surfaces. The conductive walls extend to a height above the base that is at least as large as a thickness or height of the membrane and, in particular, approximates the membrane thickness or spans the membrane. A device is adapted to apply an electric field between the conductive walls along the plane of the membrane.

The terms "in-plane electric field" are defined herein to mean an electric field in a direction along a plane in the interior of the membrane that extends along the membrane (i.e., generally parallel to the membrane surfaces). Reference in this disclosure to applying the electric field along the plane of the membrane may not require the electric field direction to be exactly parallel to the membrane surfaces. For example, in the case where the membrane is not precisely positioned flat on the wafer, the electric field may not be propagated exactly parallel to the membrane surfaces and yet this is sufficient for purposes of the invention. Similarly, when an entire cell or cells are deposited in the containment region, the cell membrane surface will have certain shape and curvature, in which case the electric field will not be applied along the plane of a membrane in all portions of the cell. This is sufficient for probing the membrane portions of the cell in which the applied electric field extends along the plane of the membrane. Finally, it will be apparent to one of ordinary skill in the art that the invention need only refer to one membrane plane as a point of reference to accurately describe application of the in-plane electric field. When the conductive walls have a height approximating a thickness or height of the membrane they span the membrane. The conductive walls may be higher if an entire biological cell or cells are positioned in the containment region compared to a molecular bilayer or monolayer positioned in the containment region. The conductive walls may span the entire height of cells or only a membrane portion of the cells positioned in the containment region.

In the second embodiment, the invention generally features a chip for probing changes in a membrane by applying an electric field. The chip includes the base and first and second electrically conductive walls spaced apart from each other and disposed on the base. The conductive walls extend approximately perpendicular to the base and parallel to each other. A first electrical conductor extends from the first conductive wall in contact with the base. A second electrical conductor extends from the second conductive wall in contact with the base. For example, the first and second electrical conductors are electrical pads fabricated on the base. The base and conductive walls form the containment region that is configured to receive the membrane. The conductive walls are configured to extend to a height above the base that is at least as large as a thickness or height of the membrane and, in particular, approximating the membrane thickness or spanning the membrane, and to propagate an electric field along the plane of the membrane.

In the third embodiment, the invention generally features a method for probing changes in a membrane by applying an electric field. The method employs the base comprised of an electrically insulative material in the containment region adapted to support one of the membrane surfaces. The electrically conductive walls are spaced apart from each other and are disposed on the base. The conductive walls extend to a height above the base that is at least as large as a thickness or height of the membrane and, in particular, approximates the membrane thickness or spans the membrane. The membrane is positioned in the containment region. An electric field is applied between the conductive walls along the plane of the membrane.

Specific features of the invention will now be described. The inventive chip may employ a flat, thin wafer of a silicon-based, electrically insulative material as the base. This base can be flat across the entire side where the conductive walls are located (i.e., a working side). On the other hand, the base can be designed to be flat in the containment region and to have other contours outside of the containment region. One particularly suitable design is to fabricate the conductive walls directly on the flat wafer. However, the addition of spacers or other articles, electrically conductive or not, on the base is considered to be part of the base. Thus, fabricating the conductive walls on the spacers or articles is a disposing of the conductive walls on the base according to this disclosure.

As defined herein the membrane can be a monolayer or bilayer comprised of amphiphilic lipids, a cell membrane or plasma membrane, one or more biological cells, a molecular monolayer, a molecular bilayer, liquid crystals and combinations thereof. The membrane can include constituents selected from the group consisting of glycolipids, phospholipids, cholesterol, proteins, and combinations thereof. While an amphiphilic lipid bilayer in a physiological liquid includes polar headgroups of the lipids forming the membrane surfaces and interior hydrophobic tails of the lipids in the membrane interior, an amphiphilic lipid bilayer in a nonaqueous liquid can be formed whereby the polar headgroups are in the interior and the hydrophobic tails extend outwardly to form the membrane surfaces.

In particular, the height of the conductive walls approximates a thickness or height of the membrane or spans the membrane, whether composed of the monolayer, bilayer, cell membrane or biological cell or cells. In particular, the membrane extends to a height of not more than 10 nanometers from the base, specifically, ranging from 5 to 10 nanometers. However, the invention contemplates using conductive walls having heights greater than the membrane thickness so long as this does not significantly interfere with application of the in-plane electric field. The spacing between the conductive walls is sufficient to accommodate the membrane sample being probed and use of an electric field of an appropriate magnitude and in particular, is not more than 10 microns, more specifically, from 3 to 10 microns. The base and conductive walls can be configured whereby the walls extend approximately perpendicular to the base and parallel to each other. The base can be flat in the containment region. An optional third electrical conductor can be fabricated between the planes of the conductive walls and does not extend above a plane of the base. The membrane is positioned in the containment region over the third electrical conductor.

In one aspect of the invention there is no cover over the containment region. This enables insertion of membrane constituents and other substances or articles, which can be used for probing or whose structural transitions upon application of the in-plane electric field can be probed. The outermost surface of the membrane located in the containment region can be contacted with an electrical conductor such as a tip of an Atomic Force Microscope ("AFM"), forming an electric field between the tip and the third electrical conductor. This advantageously permits applying an electric field to individual molecules in the membrane, such as to an individual receptor, perpendicular to the base between the tip and the third conductor. The tip of the AFM can be moved to apply the electric field to one or more membrane proteins.

The voltage source used in the apparatus is adapted to apply direct current or alternating voltage along the plane of the membrane. The voltage source can apply voltage pulses in the form of square or triangular pulses, sine wave, or other form of pulses. An electrical resistor can be connected to an electrical lead extending from the voltage source in electrical contact with one of the conductive walls. Another electrical lead in electrical contact with the other conductive wall is connected to the voltage source. A voltage drop across the resistor is monitored using an oscilloscope while varying the electric field applied along the plane of the membrane.

Referring to specific aspects of the method, in one technique the cell membrane can be contacted with a protein (e.g., the protein can be inserted in the membrane). The electric field is applied along the plane of the cell membrane and the effect of the electric field on the protein is monitored. As used herein the terms "membrane proteins" means proteins having residues that are in the lipid bilayer, proteins that span the lipid bilayer, proteins that covalently bind other proteins or molecules that are in contact with or in the bilayer, and proteins that noncovalently interact with proteins or other molecules that are in contact with or in the bilayer. All membrane proteins can be investigated using the present invention including receptor proteins, membrane transport proteins, transmembrane proteins, ion channels and combinations thereof. The investigated membrane protein can contact at least one molecule, and that molecule can directly contact the cell membrane. Alternatively, that molecule can contact another molecule that directly contacts the cell membrane.

Various techniques may be used to position the membrane in the containment region. It is desirable to achieve precise alignment of the lower membrane surface on the base and the ends of the membrane in contact with the conductive walls. In one technique, the membrane is positioned on the base in the containment region by providing liquid in the containment region, forming the membrane on the surface of the liquid, evaporating the liquid and causing the membrane to depose on the base in the containment region. In another technique the membrane is positioned on the base in the containment region by immersing the chip in a liquid, forming the membrane on the surface of the liquid, lifting the base from the liquid causing the liquid to leave the containment region, and causing the membrane to depose on the base in the containment region.

The present invention offers numerous advantages. The invention enables probing of membranes by applying the in-plane electric field, which heretofore was not possible. The invention permits investigating membrane systems on the scale of a monolayer or bilayer, which will uncover behavior that may not be observable in bulk. One particularly valuable aspect of the invention is its ability to analyze the cell membrane with extreme versatility. Various cell membranes can be used from various cell and tissue types, conditions and environments. The membrane can be formed so that its composition is known. The specific lipids can be extracted and purified from existing membranes and used in the sample membrane. Specific proteins can be inserted one at a time at particular locations in the membrane. These proteins can be inserted at isolated locations or at locations near other proteins to enable probing of their interaction. On the other hand, the invention offers the flexibility of designing the sample membrane with a plurality of proteins. The membrane can be made to include a variety of different proteins and other membrane constituents. The sample membrane can be a portion of an actual biological cell membrane. In addition, one or more entire cells can be positioned in the containment region and the structural changes of their cell membranes that comprise the membrane in the containment region, can be probed. Other membranes can be probed in the invention, ideally on the scale of a molecular monolayer or bilayer. For example, liquid crystal molecules, biological or non-biological, can be positioned in the containment region on the base and probed in accordance with the present invention.

The membrane can be probed in a variety of ways. Because the containment region can be without a cover, the membrane can be physically contacted before, during and after application of the in-plane electric field. For example, the tip of an atomic force microscope can be scanned over the exposed outermost membrane surface in the containment region. Microscopy of the membrane can also be carried out, for example, using one or more of the following: confocal microscope, laser scanning confocal microscope, scanning electron microscope, transmission electron microscope, phase contrast microscope, differential-interference-contrast microscope, dark-field microscope, bright-field microscope, electron microscope tomography, and fluorescence microscope. The invention enables a thorough evaluation of the various properties of the membrane, including topographical, electrical, viscous, and elastic properties. The membrane also can be positioned so that it can be accessed from one or two sides of the containment region. This offers additional probing, for example, using X-ray spectroscopy. Another instrument that can be used to probe the membrane is an impedance gain phase analyzer.

Not only can changes in the membrane be probed by applying the electric field, but the membrane can be treated and a response to the treatment can be observed. For example, the membrane can be subjected to a treatment including but not limited to: drug, therapeutic, chemical, enzymatic, ligand, fluorescence, small interfering RNA ("siRNA"), antisense RNA, hormonal, antibody, viral, bacterial and parasitic treatments, and combinations thereof. As a particular example, one can investigate the capillary endothelial cells of the blood brain barrier and response to certain therapeutics upon manipulation of protein carriers or transporters by applying the in-plane electric field and/or by applying the electric field between the tip of the atomic force microscope and the third conductor. One can probe cancer cells and monitor their response to certain chemical compounds of interest, such as anticancer drugs, with and without application of the in-plane electric field.

The treatment of the membrane can be carried out before, during or after probing of the membrane by application of the in-plane electric field. The membrane may be treated while in the containment region or before being placed in the containment region. The invention can be used to investigate cellular transport or signaling. It may be possible to manipulate cellular receptors of a membrane in the containment region, to change their conformation from an open conformation capable of binding ligands to a closed conformation incapable of binding ligands, by application of the in-plane electric field to the membrane and/or by application of the electric field between the AFM tip and the third electrical conductor. This change in the receptor conformation may be probed with the AFM or other instruments.

In view of the use of the present invention with biological cell membranes and biological cells, the wafers can be sterilized and packaged in a sterile condition.

The membrane treatment can be combined with the various probing techniques including, but not limited to, probing of chemical, electric, viscous, elastic, and topographical properties. For example, certain proteins of interest can be fluorescently tagged, inserted into the cell membrane and then monitored using a fluorescence microscope. Their topographical structural transitions can be observed using an AFM, upon application of the electric field.

It is advantageous for a chip to include a plurality of containment regions so that multiple experiments can be conducted at one time using the chip. Each chip is disposable after use. The containment regions can be electrically addressed with the in-plane electric field all at the same time by electrically interconnecting the conductive walls of the chip. On the other hand, the chip can be fabricated in a way that enables the containment regions to be electrically independently addressed with the in-plane electric field at different times and different voltages. One of ordinary skill in the art will recognize that these are but a few examples of innumerable applications of the present invention.

DETAILED DESCRIPTION

Figure 1:
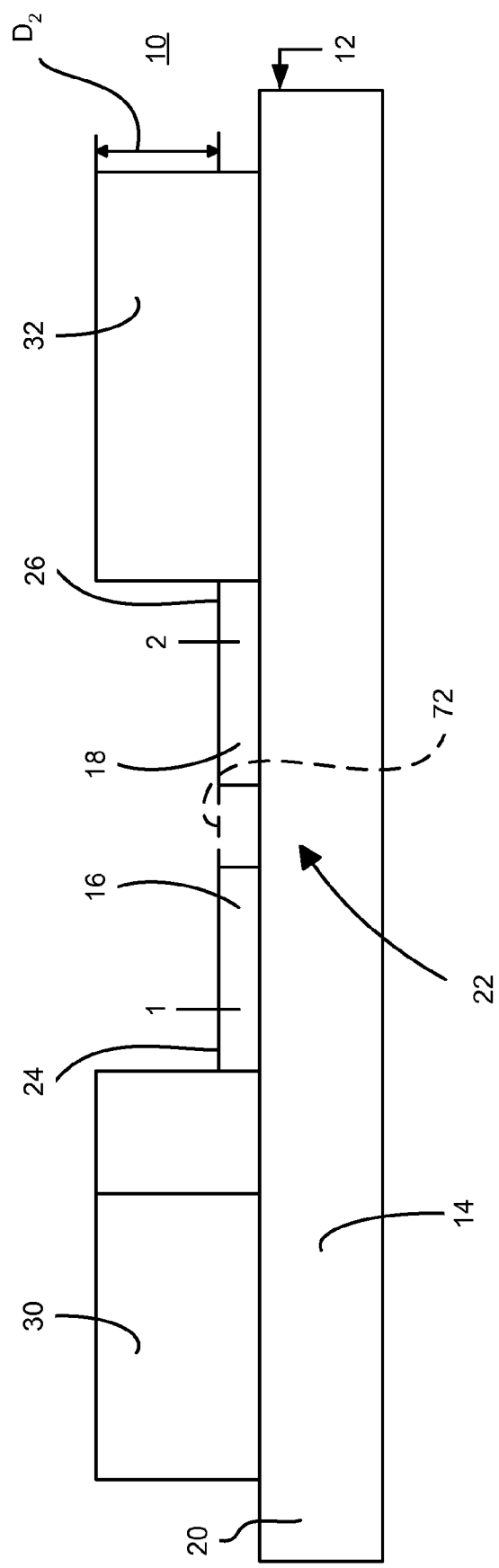
FIG. 1 is a side view of a chip constructed in accordance with the present invention.
Figure 2:
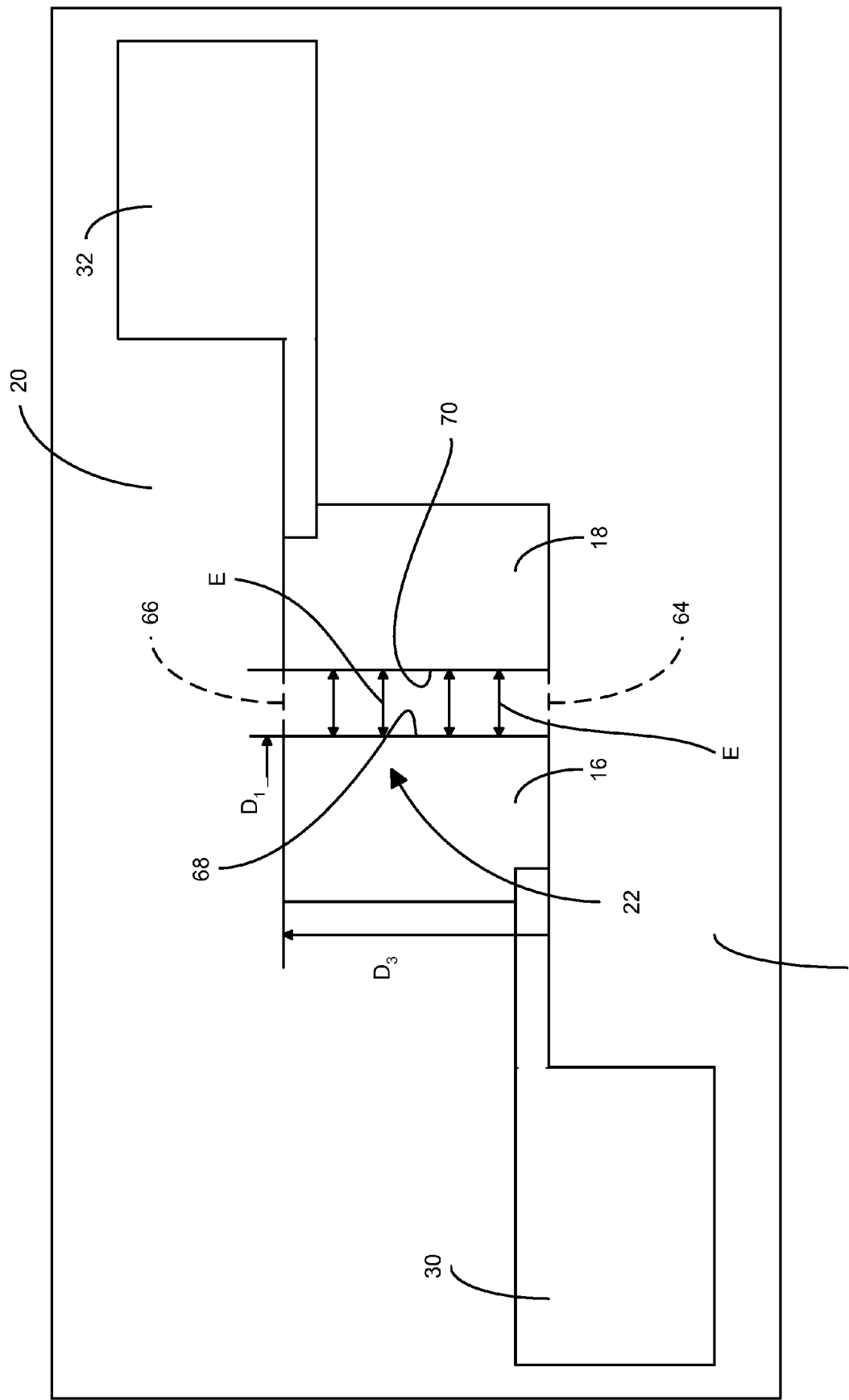
FIG. 2 is a top plan view of the inventive chip of FIG. 1.

Referring now to the drawings, the invention features an apparatus 10 including a chip 12 having an electrically insulating thin wafer 14 as a base on which first and second nanometer scale electrically conducting walls 16, 18 are fabricated. The wafer has a flat upper or working surface 20. The conductive walls 16, 18 extend approximately perpendicular to the base and are spaced apart approximately parallel to each other by a distance D1. A containment region or volume 22 has a width defined between the conductive walls 16, 18 at distance D1, a height D2 defined between the surface 20 of the wafer 14 in the containment region and upper surfaces 24, 26 of the conductive walls, and a length D3 defined by a length of the conductive walls. Electrically conducting pads 30, 32 extending from the electrically conducting walls 16, 18, respectively, are also fabricated on the wafer 14. Electrical leads 34, 36 from a voltage source 38 (FIG. 3) are connected to the electrical conducting pads 30, 32, respectively, enabling application of a voltage to the conductive walls that propagates an electric field E between the electrical conducting walls in a direction that is perpendicular to them (shown by arrows in FIGS. 1-3).

Figure 5:
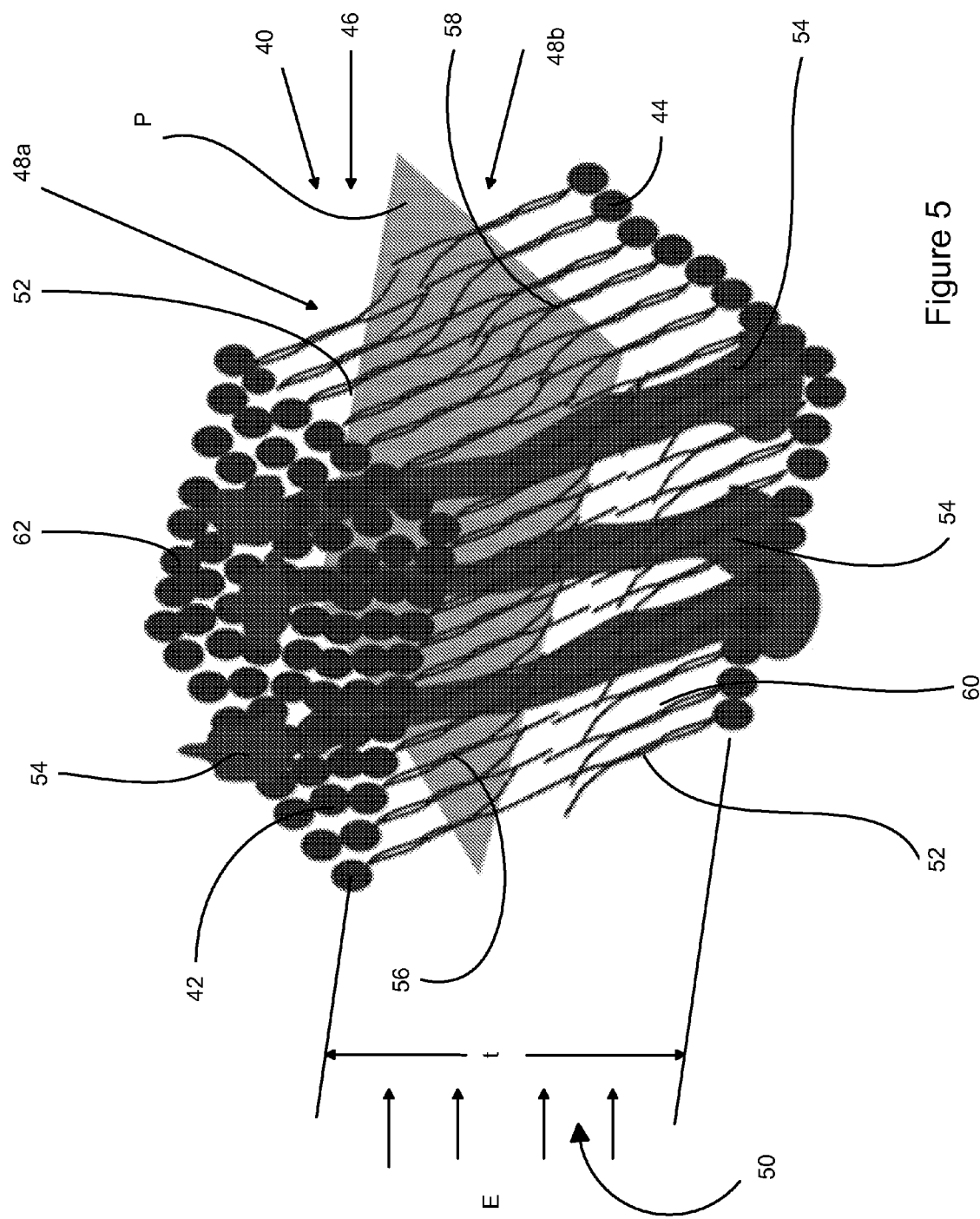
FIG. 5 is a perspective view of a membrane comprised of a lipid bilayer that is used in the present invention.

Referring to FIG. 5, a membrane 40 is disposed in the containment region 22 and has opposing spaced apart-surfaces 42, 44 that extend across a major area of the membrane, an interior 46 between these surfaces and a thickness or height t. An interior plane P of the membrane is bounded by the membrane surfaces and extends along the membrane (i.e., approximately parallel to the membrane surfaces). It should be appreciated that certain membranes, as in the case of the biological cell membrane, have an inner membrane surface and an outer membrane surface, which may have different relative localized compositions and concentrations of proteins and other constituents, ion gradients and the like. The sample membrane can comprise a monolayer 48a or 48b or a bilayer 50 (including layers 48a and 48b) of natural amphiphilic lipids 52 found in the biological cell membrane including glycolipids, phospholipids, synthetic amphiphilic lipids, other constituents of the biological cell membrane including cholesterol and proteins (e.g., transmembrane proteins 54), and liquid crystal molecules and any combination of them. Any of these constituents can be added any time after the initial membrane is formed in the containment region. The invention is suitable for probing membranes of any chemical composition, even non-biological membranes. A portion of a biological cell membrane can be deposited in the containment region. An entire biological cell or cells may be deposited in the containment region, which forms the membrane in the containment region as that term is used in this disclosure.

The bilayer can be formed by extracting and purifying amphiphilic lipids from biological cell membranes and using these lipids to form the bilayer. Other cell membrane constituents, such as cholesterol and proteins, can be extracted and inserted one or more molecules at a time into the lipid bilayer. The membrane constituents can be inserted into the bilayer before or after application of the electric field. For example, in the case of probing the structural changes of a particular protein of interest (e.g., a transmembrane protein or receptor protein), one or a limited number of proteins can be inserted and then their response to the in-plane field can be monitored. The bilayer can be formed by combining one or more chemically or enzymatically synthesized molecules (e.g., proteins) and structural transitions of the membrane constituents can be probed upon application of the in-plane electric field.

The electrically conductive walls 16, 18 are disposed on the wafer and extend upwardly to a height D2 that is at least as high as the thickness or height t of the membrane in the containment region (i.e., the distance between the upper membrane surface and the base in a direction perpendicular to the base). In particular, the conductive walls can have a height D2 that approximates the thickness t of the membrane, for example, a height in a range of 5 to 10 nanometers from the surface 20 of the nonconductive wafer 14. The conductive walls can have a height D2 approximating the thickness of a molecular monolayer or bilayer, a biological cell membrane, or biological cell or cells, positioned in the containment region. The distance D1 between the conductive walls 16, 18 can vary as desired to accommodate the membrane sample. For example, the distance is in a range of about 3 to 10 micrometers.

When the membrane 40 is deposited in the containment region 22, the lowermost membrane surface 44 is in contact with surface 20 of the wafer 14 while the uppermost membrane surface 42 is exposed to probing. The wafer 14 supports and stabilizes the membrane in the containment region. Two sides of the membrane (e.g., sides 56, 58) are in contact with the conductive walls 16, 18. One or both of the other sides of the membrane 60, 62 can also be exposed to probing near side limits 64, 66 of the containment region.

Figure 3:
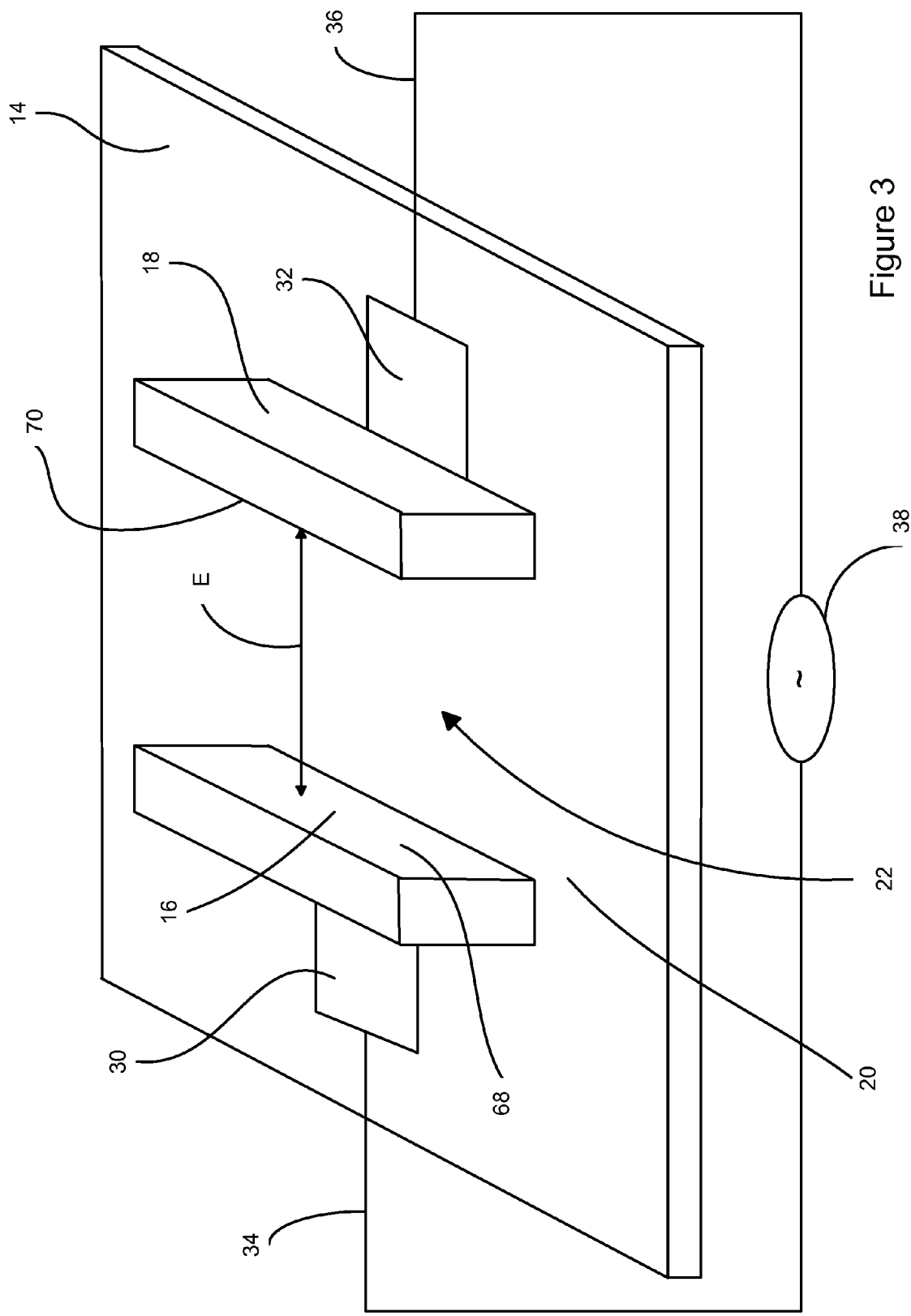
FIG. 3 is a perspective view of an apparatus constructed in accordance with the present invention.

Referring to FIG. 3, the voltage source 38 applies an electric field E along the plane P of the membrane 40 when the membrane surface 44 is disposed on the wafer 14 and the membrane sides 56, 58 contact inner surfaces 68, 70 of the conductive walls 16, 18. It is desirable to position or depose the membrane flat on the wafer. This assists in probing the exposed upper surface 42 of the membrane at a known location. In addition, as the conductive walls are perpendicular to the wafer, the electric field E can be applied along the plane of the membrane P.

The containment region 22 advantageously is exposed or uncovered on its top limit 72 and in particular, on one or two of its side limits 64, 66 as well. An advantage of the invention is that it enables probing of the top surface of the membrane and, optionally, sides of the membrane. In addition, the open top of the containment region permits adding any component to the membrane before, during and after application of an electric field, including but not limited to membrane constituents.

Figure 4:
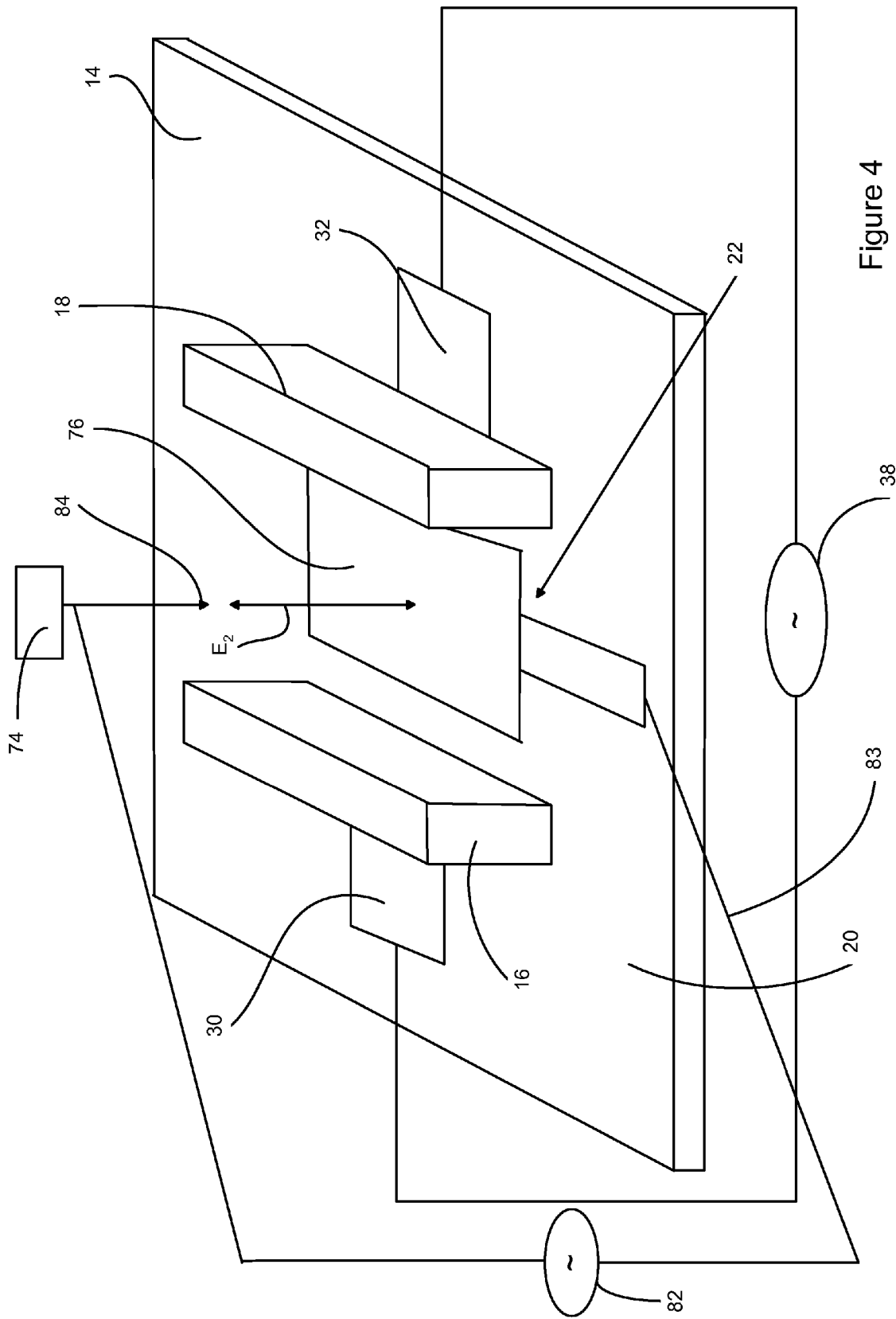
FIG. 4 is a perspective view of another aspect of the inventive apparatus.

One particularly suitable instrument of the inventive apparatus 10 for probing the membrane is an Atomic Force Microscope ("AFM") 74 generally shown in FIG. 4, which is capable of detecting structural changes or transitions of the membrane constituents. The atomic force microscope and other instruments are able to physically detect the membrane through the open top or sides before, during, and after an electrical field is applied in the device. Of course, while the open top or sides of the containment region is an advantageous feature of the present invention, one of ordinary skill in the art will appreciate in view of this disclosure that a cover for the open top or sides of the containment region is desirable in some instances. For example, a cover (e.g., glass or plastic coverslip) might be placed on top of the conductive walls before, after, and in some cases during, microscopy to prevent any contamination or to prevent drying of the membrane.

The voltage source 38 is adapted to apply voltages to the conductive walls, which propagates an electric field E therebetween, perpendicular to the walls and along the plane P of the membrane when the lower membrane surface is disposed flat on the wafer in the containment region. The voltage source may apply a direct current or alternating voltage to the conductive walls. The voltage source can apply voltage pulses to the conductive walls, for example, square pulses, triangular pulses, and sine wave. The magnitude of the voltage pulse, determined by pulse width and amplitude, can be selected by one of ordinary skill in the art in view of this disclosure. The voltages will be applied at suitable magnitudes for causing structural changes to the constituents of the membrane.

The inventive chip can include one or more containment regions 22. The voltage source can electrically address the conductive walls of each containment region with the same or different voltage magnitudes and at the same or different time. In addition, the voltage source can apply voltage to containment regions on different chips at the same or different time. The membranes that are positioned in the multiple containment regions can be the same or different. For example, some containment regions of a chip can include bilayers, other containment regions of the chip can include cells and still other containment regions of the chip can include cell membranes; or all containment regions of the chip can include cell membranes but from different cell or tissue types or subject to different treatments.

The first conducting wall 16 and the second conducting wall 18 can be made of any electrical conducting material, for example, Au, Ag or Cu but not limited to these.

The wafer is made of electrically insulative materials, for example, $Si/SiO_2$ but not limited to these.

Figure 6:
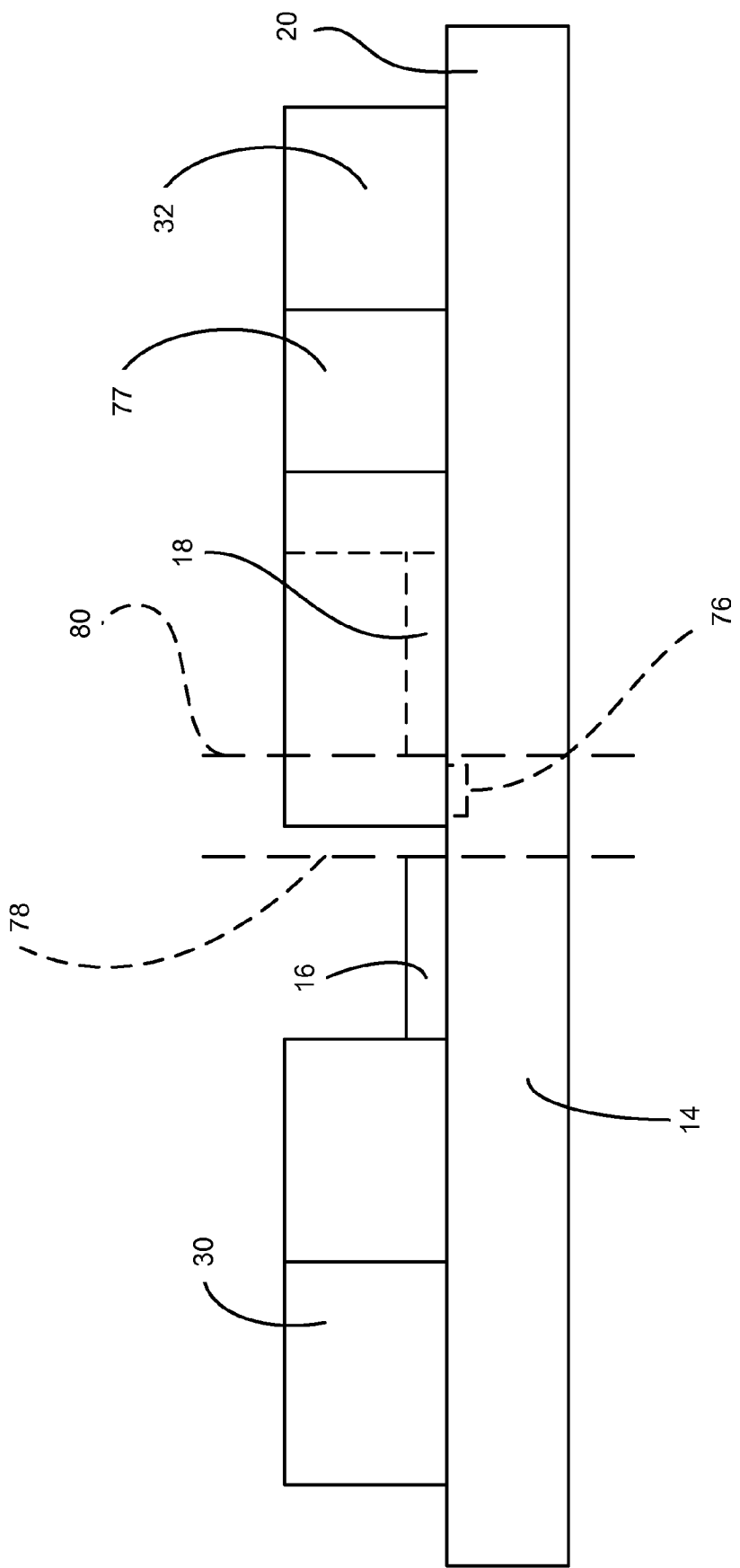
FIG. 6 is a side view of a chip constructed in accordance with the present invention, showing a third electrical conductor between the planes of conductive walls and below a plane of a base.
Figure 7:
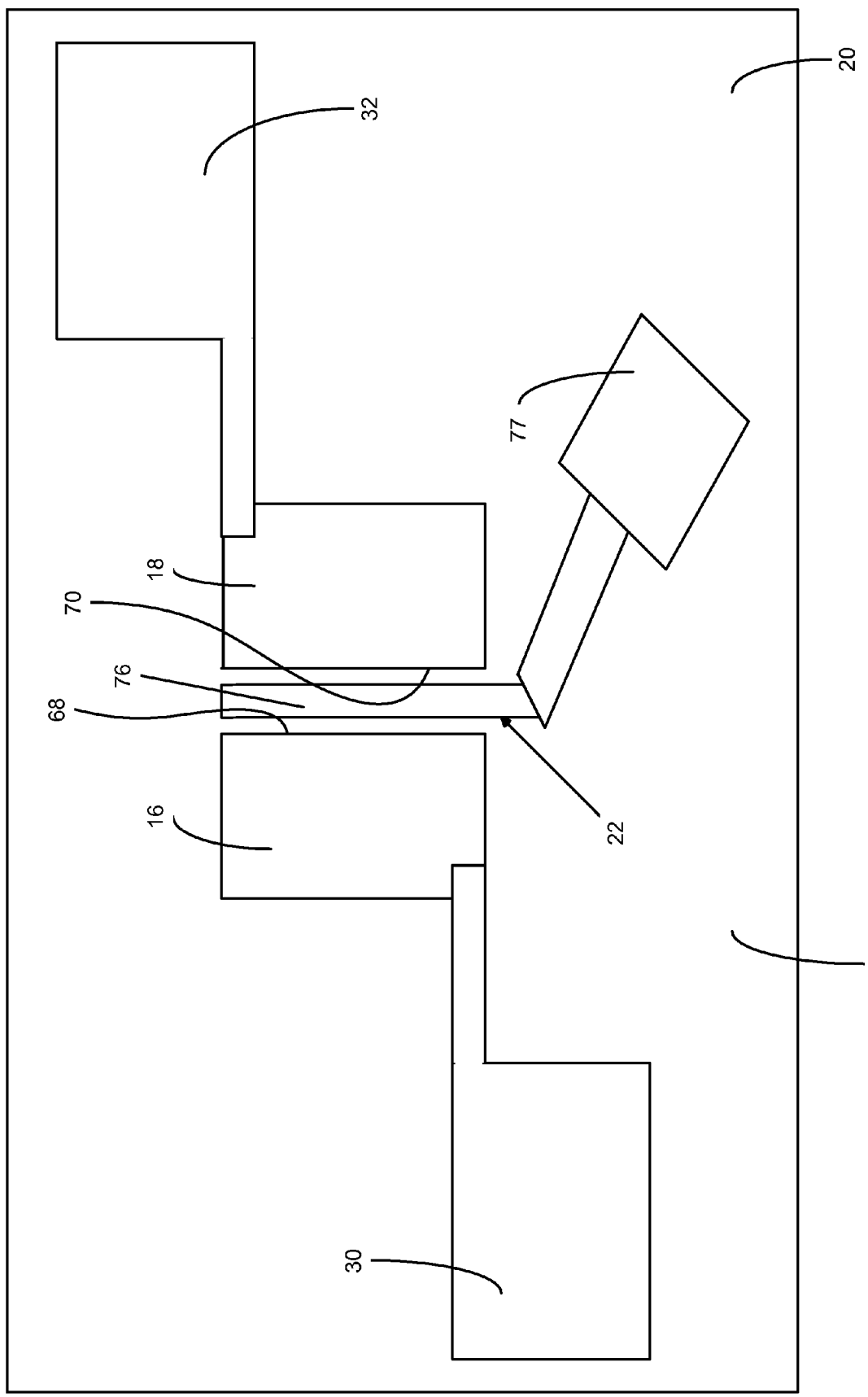
FIG. 7 is a top plan view of the chip shown in FIG. 6.

Referring to FIGS. 6 and 7 an optional third electrode 76 is fabricated in between a plane 78 of the inner surface 68 of the first conducting wall 16 and a plane 80 of the inner surface 70 of the second conducting wall 18. The plane of this third electrode 76 does not extend above the surface 20 of the electrically insulative wafer into the containment region 22. The third electrode 76 is spaced from the conductive walls 16, 18 so as to be electrically isolated therefrom. An electrically conductive pad 77 is fabricated on the wafer and in electrical contact with the third electrode 76. The third electrode 76 and conductive pad 77 can be made of any electrical conducting material, for example, Au, Ag or Cu but not limited to these.

A voltage source 82 can apply a voltage to the third electrode via lead 83. An electric field E2 may thus be established between an electrode such as the tip 84 of the atomic force microscope 74 (represented by an arrow in FIG. 4) and the third electrode 76. The electric field E2 extends through the sample membrane in a direction perpendicular to the base.

Figure 8:
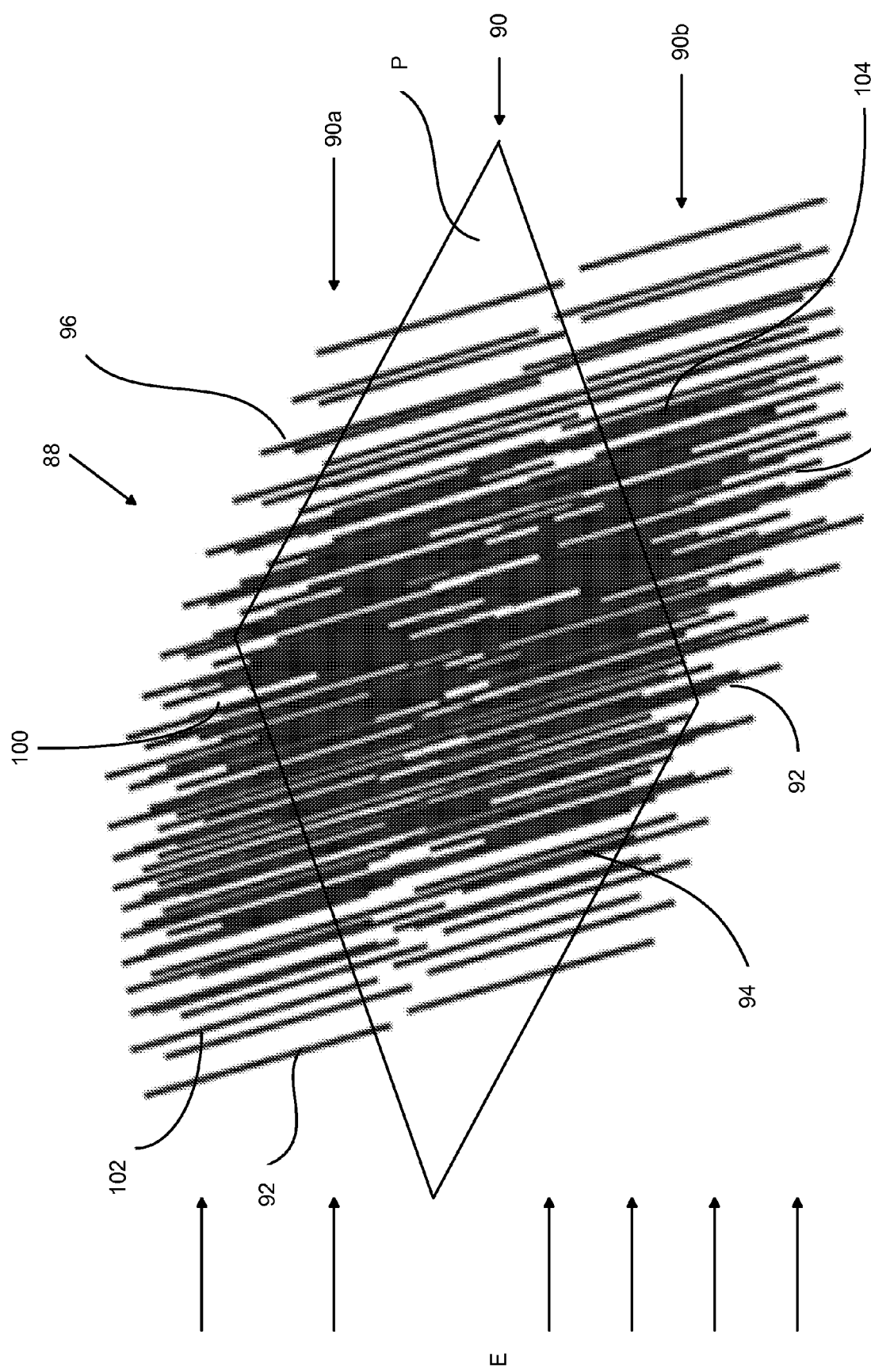
FIG. 8 is a perspective view showing an example of another membrane used in the present invention.
Figure 9:
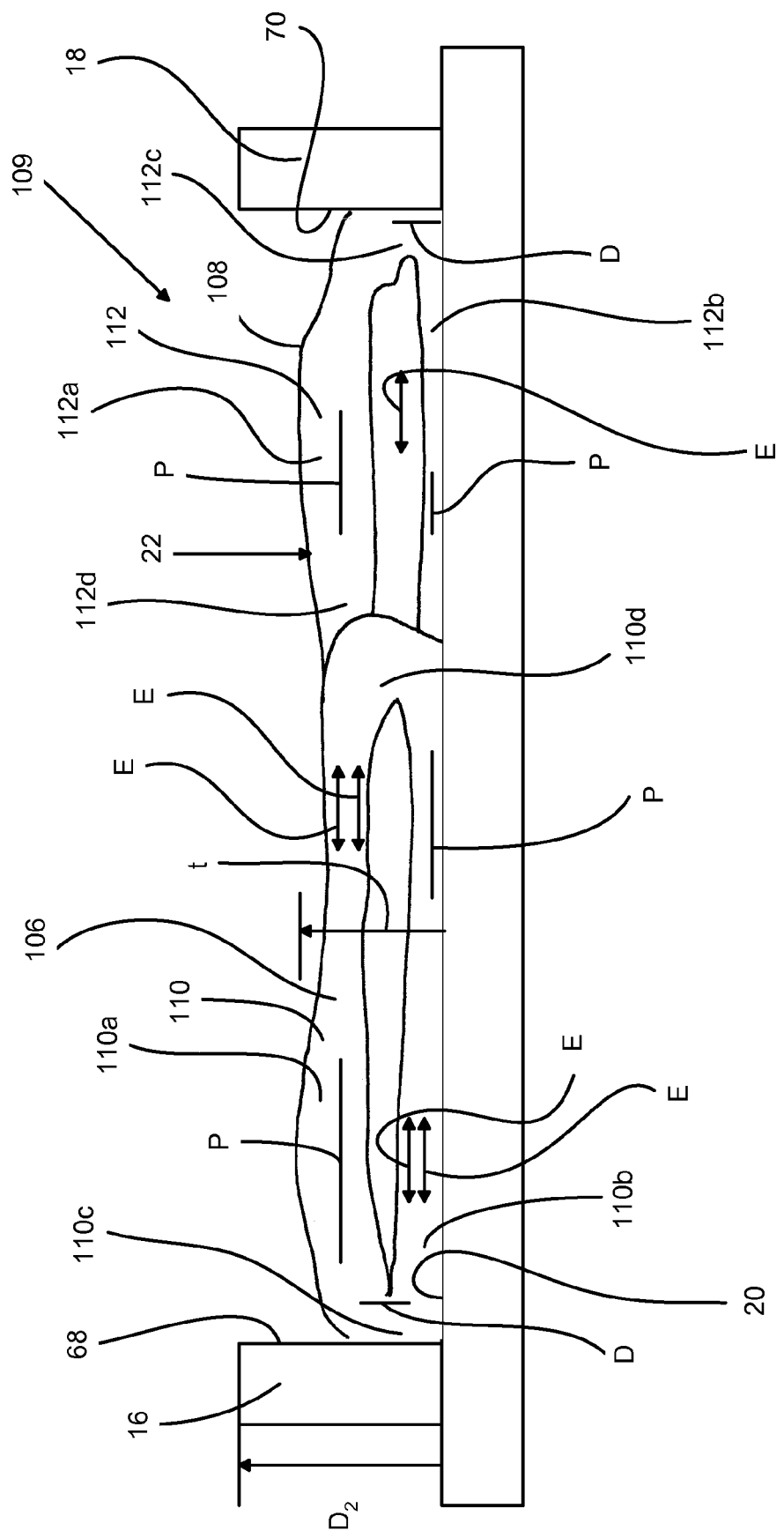
FIG. 9 is a side view of the inventive chip in which the membrane being probed is formed by biological cells. These cells are shown with the cell membrane having exaggerated thickness to improve understanding of the present invention.

FIGS. 8 and 9 depict other examples of membranes used in the present invention. FIG. 8 depicts a membrane 88 comprised of a bilayer 90 of molecules 92 such as liquid crystal molecules. These molecules 92 can be oriented perpendicular or tilted relative to the surface 20 of the wafer 14, for example. The bilayer includes molecular layers 90*a* and 90*b* that are stacked over each other. Either molecular monolayer 90*a* or molecular monolayer 90*b* can be separately probed as a membrane in accordance with the invention. In the specific example shown, the membrane has a configuration as it would be deposed in the containment region, including sides 94 and 96 that contact the inner surfaces 68, 70, respectively, of the conductive walls 16, 18, a lower surface 98 that contacts the surface 20 of the base 14 in the containment region 22, an upper surface 100 that is exposed to probing, and outer surfaces 102, 104 corresponding to side limits 66, 64 of the containment region that are exposed to probing. The voltage source 38 applies voltage to the conductive walls 16, 18 and an electric field E is propagated perpendicular to the walls in a direction along a plane of the membrane P. The plane P extends approximately parallel to upper and lower surfaces 100, 98.

As another example, FIG. 9 shows two cells 106, 108 deposed on the flat surface 20 of the base 14 in the containment region 22. The cells include plasma membranes 110, 112 around their periphery each formed of a lipid bilayer and membrane constituents including phospholipids, glycolipids, cholesterol and proteins. As positioned in the containment region, the cells include an exposed upper membrane portion 110a, 112a and a lower membrane portion 110b, 112b. The plasma membranes of cells 106, 108 compose a "membrane" 109 spanning the containment region 22 as that term is used in this disclosure. The cells also include outer side membrane portions 110c, 112c and inner side membrane portions 110d, 112d. The lower membrane portions 110b, 112b are generally flat in contact with the flat surface 20 of the electrically insulative wafer 14. The inner side membrane portions 110d and 112d may contact each other. The outer side membrane portions 110c, 112c contact the inner surfaces 68, 70 of the conductive walls 16, 18, respectively. The conductive walls 16, 18 have a height D2 that approximates the thickness or height t of the cells in the containment region. An electric field E is propagated between the conductive walls in a direction along planes P of each bilayer portion. While the conductive walls are shown having a height D2 that spans the entire height of the cells, it will be appreciated that the conductive walls may be disposed on an electrically insulative article that is fabricated on the base such that the conductive walls span only the upper portions 110a, 112a of the cell membrane. While side portions 110c, 112c of the plasma membranes have planes D that are not generally parallel to the plane of the surface 20 of the base, the cells can be probed with regard to the cell membrane portions that do have planes P along which the electric field E extends, perpendicular to the conductive walls 16, 18.

Structural transitions in the membrane and the proteins embedded in or in contact with the membrane are caused by the reorientation of the lipid molecules coupled to the in-plane electric field.

Structural changes to the membrane in response to application of the in-plane electric field are probed by electric current measurements, atomic force microscope, confocal microscope, confocal laser scanning microscope, fluorescence microscope and X-ray spectrometer, but not limited to these tools.

Viscous, elastic and electric properties of the membrane can be measured in accordance with the invention.

Many modifications and variations of the invention will be apparent to those of ordinary skill in the art in light of the foregoing disclosure. Therefore, it is to be understood that, within the scope of the appended claims, the invention can be practiced otherwise than has been specifically shown and described.

What is claimed is:

1. A method for probing changes in a membrane by applying an electric field, comprising:
providing a base, electrically conductive walls spaced apart from each other and disposed on said base, wherein said conductive walls and said base form a containment region that is configured to receive a membrane, said membrane having opposing top and bottom membrane surfaces and an interior reference plane that is bounded by said membrane surfaces and extends along said membrane, and said membrane having side surfaces, said base being comprised of an electrically insulative material in said containment region, wherein said conductive walls extend to a height above said base that is at least as large as a thickness of said membrane;
wherein said membrane is selected from the group consisting of: a monolayer or bilayer comprised of amphipathic lipids, a cell membrane, at least one biological cell, a molecular bilayer, liquid crystals and combinations thereof;
positioning said membrane in said containment region so as to contact said side surfaces of said membrane with said conductive walls and said bottom surface of said membrane flat in contact with said base in said containment region;
applying an electric field between said conductive walls along the plane of said membrane; and
using microscopy to monitor changes in said membrane caused by application of said electric field.

2. The method of claim 1 wherein said base is flat in said containment region and said conductive walls are approximately perpendicular to said base and parallel to each other, said conductive walls having a height approximating a thickness of said membrane.

3. The method of claim 1 wherein said conductive walls have a height above said base of not more than 10 nanometers.

4. The method of claim 1 wherein said microscopy is atomic force microscopy.

5. The method of claim 4 comprising contacting a surface of said membrane with a tip of said atomic force microscope.

6. The method of claim 1 further comprising probing or visualizing said membrane using an instrument selected from the group consisting of: confocal microscope, laser scanning confocal microscope, scanning electron microscope, transmission electron microscope, phase contrast microscope, differential-interference-contrast microscope, dark-field microscope, bright-field microscope, electron microscope tomography, fluorescence microscope, X-ray spectrometer and impedance gain phase analyzer.

7. The method of claim 1 comprising measuring properties of said membrane selected from the group consisting of: topographical, electrical, viscous, elastic properties, and combinations thereof.

8. The method of claim 1 wherein said membrane is positioned on said base in said containment region by providing liquid in said containment region, forming said membrane on a surface of the liquid, evaporating the liquid and causing said membrane to depose on said base in said containment region.

9. The method of claim 1, wherein said membrane is positioned on said base in said containment region by immersing said base in liquid, forming said membrane on a surface of the liquid, lifting said base from said liquid causing said liquid to leave said containment region and causing said membrane to depose on said base in said containment region.

10. The method of claim 1 comprising applying said electric field to said membrane as voltage pulses.

11. The method of claim 10 wherein said voltage pulses are selected from the group consisting of square pulses, triangular pulses, and sine wave.

12. The method of claim 1 wherein said membrane includes constituents selected from the group consisting of glycolipids, phospholipids, cholesterol, proteins, and combinations thereof.

13. The method of claim 1 comprising connecting an electrical resistor to an electrical lead extending from a voltage source in electrical contact with one of said conductive walls and connecting another electrical lead in electrical contact with the other said conductive wall to said voltage source and monitoring a voltage drop across said resistor using an oscilloscope while varying the electric field applied along the plane of said membrane.

14. A method for probing changes in a membrane in response to treating said membrane with an agent by applying an electric field, comprising:
   providing a base, electrically conductive walls spaced apart from each other and disposed on said base, wherein said conductive walls and said base form a containment region that is configured to receive a membrane, said membrane having opposing top and bottom membrane surfaces and an interior reference plane that is bounded by said membrane surfaces and extends along said membrane, and said membrane having side surfaces, said base being comprised of an electrically insulative material in said containment region, wherein said conductive walls have a size approximating a thickness of said membrane;
   wherein said membrane is selected from the group consisting of: a monolayer or bilayer comprised of amphipathic lipids, a cell membrane, at least one biological cell, a molecular bilayer, liquid crystals and combinations thereof;
   positioning said membrane in said containment region so as to contact said side surfaces of said membrane with said conductive walls and said bottom surface of said membrane flat in contact with said base in said containment region;
   Applying an electric field between said conductive walls along the plane of said membrane;
   treating said membrane with said agent selected from the group consisting of: drug, therapeutic, chemical, enzyme, ligand, fluorescence, siRNA, antisense RNA, hormone, antibody, virus, bacteria, parasites, and combinations thereof;
   and using microscopy to observe a response to said treatment.

15. The method of claim 1 comprising inserting a protein into said cell membrane, applying said electric field along the plane of said cell membrane and using said microscopy to monitor the effect of said electric field on said protein.

16. The method of claim 1 comprising using said microscopy to monitor an effect of said electric field on a protein of said membrane.

17. The method of claim 16 wherein said protein contacts at least one molecule, and said molecule directly contacts said cell membrane or said molecule contacts another molecule that directly contacts said cell membrane.

18. The method of claim 16 wherein said protein is selected from the group consisting of a receptor protein, a membrane transport protein, a transmembrane protein, an ion channel and combinations thereof.

19. A method for probing changes in a protein that contacts a membrane by applying an electric field, comprising:
   providing a base, electrically conductive walls spaced apart from each other and disposed on said base, wherein said conductive walls and said base form a containment region that is configured to receive a membrane, said membrane having opposing top and bottom membrane surfaces and an interior reference plane that is bounded by said membrane surfaces and extends along said membrane, and said membrane having side surfaces, said base being comprised of an electrically insulative material in said containment region, wherein said conductive walls have a size approximating a thickness of said membrane;
   wherein said membrane is selected from the group consisting of: a monolayer or bilayer comprised of amphipathic lipids, a cell membrane, at least one biological cell, a molecular bilayer, liquid crystals and combinations thereof;
   positioning said membrane in said containment region so as to contact said side surfaces of said membrane with said conductive walls and said bottom surface of said membrane fiat in contact with said base in said containment region;
   applying an electric field between said conductive walls along the plane of said membrane;
   contacting said membrane with said protein; and
   using microscopy to monitor an effect on said protein that contacts said membrane caused by application of said electric field.

20. The method of claim 19, wherein said contacting comprises inserting said protein in to said cell membrane.

21. The method of claim 19 wherein said protein is selected from the group consisting of a receptor protein, a membrane transport protein, a transmembrane protein, an ion channel and combinations thereof.

22. The method of claim 19 comprising contacting a surface of said membrane with a tip of an atomic force microscope.

23. The method of claim 19 comprising treating said membrane and observing a response to said treatment, wherein said treatment is selected from the group consisting of: drug, therapeutic, chemical, enzymatic, ligand, fluorescence, siRNA, antisense RNA, hormonal, antibody, viral, bacterial and parasitic treatments, and combinations thereof.

* * * * *

UNITED STATES PATENT AND TRADEMARK OFFICE
CERTIFICATE OF CORRECTION

PATENT NO. : 7,674,610 B2 Page 1 of 1
APPLICATION NO. : 11/400685
DATED : March 9, 2010
INVENTOR(S) : Thusara Sugat Chandra Abeygunaratne It is certified that error appears in the above-identified patent and that said Letters Patent is hereby corrected as shown below:

On the title page, please include the Related U.S. Application Data Item (60) section and insert
--Provisional application No. 60/669,496, filed Apr. 8, 2005.--

Signed and Sealed this

Twenty-seventh Day of July, 2010

David J. Kappos
*Director of the United States Patent and Trademark Office*